United States Patent
Schmidt et al.

(10) Patent No.: US 7,087,181 B2
(45) Date of Patent: Aug. 8, 2006

(54) METHOD FOR FABRICATING MICRO-STRUCTURES WITH VARIOUS SURFACE PROPERTIES IN MULTI-LAYER BODY BY PLASMA ETCHING

(75) Inventors: Walter Schmidt, Russikon (CH); Frédéric Reymond, La Conversion (CH); Joël S. Rossier, Saillon (CH)

(73) Assignee: DiagnoSwiss S.A., Monthey (CH)

( * ) Notice: Subject to any disclaimer, the term of this patent is extended or adjusted under 35 U.S.C. 154(b) by 152 days.

(21) Appl. No.: 10/182,577

(22) PCT Filed: Jan. 30, 2001

(86) PCT No.: PCT/CH01/00070

§ 371 (c)(1),
(2), (4) Date: Oct. 18, 2002

(87) PCT Pub. No.: WO01/56771

PCT Pub. Date: Aug. 9, 2001

(65) Prior Publication Data

US 2003/0102284 A1    Jun. 5, 2003

(51) Int. Cl.
*B81C 1/00* (2006.01)

(52) U.S. Cl. ............................. 216/39; 216/65; 216/67
(58) Field of Classification Search .................. 216/67
See application file for complete search history.

(56) References Cited

U.S. PATENT DOCUMENTS

| | | | | |
|---|---|---|---|---|
| 5,992,820 A | * | 11/1999 | Fare et al. | 251/129.01 |
| 6,103,199 A | * | 8/2000 | Bjornson et al. | 422/100 |
| 6,355,491 B1 | * | 3/2002 | Zhou et al. | 436/518 |
| 6,423,465 B1 | * | 7/2002 | Hawker et al. | 430/203 |
| 6,756,019 B1 | * | 6/2004 | Dubrow et al. | 422/102 |
| 2003/0113528 A1 | * | 6/2003 | Moya | 428/304.4 |
| 2004/0115833 A1 | * | 6/2004 | Sudor | 436/514 |

FOREIGN PATENT DOCUMENTS

WO    WO 92 15408 A    9/1992

OTHER PUBLICATIONS

*International Preliminary Examination Report* dated May 27, 2002.

* cited by examiner

*Primary Examiner*—Allan Olsen
(74) *Attorney, Agent, or Firm*—Robert E. Bushnell, Esq.

(57) ABSTRACT

The technology is based on the anisotropic plasma etching of organic polymer sheets partially protected by a metallic mask. The originality of the process is to pattern the surface properties by the same physical means as the one used for the three dimensional fabrication and simultaneously to this fabrication. Surface properties means, but are not limited to hydrophobicity, hydrophilicity, conductivity, reflectability, rugosity and more precisely the chemical and/or physical state of the surface. It is also possible to generate the desired fonctionalities, for instance carboxylic acid, ester, ether, amid or imid, during the etching process. The patterning of the different properties may be achieved by two different techniques that may be used separately or simultaneously.

41 Claims, 10 Drawing Sheets

METHOD FOR FABRICATING MICRO-STRUCTURES WITH VARIOUS SURFACE PROPERTIES IN MULTI-LAYER BODY BY PLASMA ETCHING

CLAIM FOR PRIORITY

This application makes reference to, incorporates the same herein, and claims all benefits accruing under 35 U.S.C. §§119 from a provisional application for METHOD FOR FABRICATING MICRO-STRUCTURES WITH VARIOUS SURFACE PROPERTIES I MULTILAYER BODY BY PLASMA ETCHING earlier filed under 35 U.S.C. §111(b) in the United States Patent & Trademark Office on the 31 Jan. 2000 and there duly assigned Ser. No. 60/179,334.

CROSS-REFERENCE TO RELATED APPLICATIONS

This application refers to and relates to a Patent Cooperation Treaty application entitled METHOD FOR FABRICATING MICRO-STRUCTURES WITH VARIOUS SURFACE PROPERTIES IN MULTI-LAYER BODY BY PLASMA ETCHING filed in the World Intellectual Property Organization via the Swiss Federal Institute of Intellectual Property on the $30^{th}$ day of Jan. 2001, and there assigned Application No. PCT/CH01/00070, and later published as publication No. WO 01/56771 A2 on the $9^{th}$ day of Aug. 2001.

FIELD OF THE INVENTION

The present invention provides a fabrication method for the three dimensional structuration and patterning of at least two different surface properties for micro-systems or micro-substrates.

BACKGROUND OF THE INVENTION

Over the last ten years, a general effort towards miniaturization of the analytical tools has been observed. Two main reasons are pushing the development miniaturized chemical apparatus, which have been called Micro Total Analysis Systems (µ-TAS): a decrease of analyte consumption and a decrease of duration of single analysis. Both needs are particularly evident in the new development of life science, where genetic analysis and high throughput screening in drug discovery take more and more importance. In these applications, the reason for limiting the analyte consumption are evidenced by the increasing number of performed assays. In this case, the use of reactants for analysis must be as small as possible in order not only to reduce the cost but also to limit the waste production. In other cases, the analysis of extremely small volumes is required. Such a volume may be only a few nL, e.g. in the case of neurological fluid analysis or in prenatal diagnostics. In many cases, the decrease in analysis time is also an important issue e.g. in medical diagnostics, where the time factor may signify a fatal issue for the patient. Two different and complementary strategies have been developed in parallel to achieve these goals. On one hand, the fabrication of microfluidic devices has allowed fluid handling in pL volumes and, on the other hand, immobilization of affinity reagents into high density 2-dimensional arrays for high throughput affinity analysis.

In recent years, capillary electrophoretic methods have enjoyed gaining popularity, primarily due to the observed high separation efficiencies, peak resolution, and wide dynamic ranges of molecular weights that may be analyzed. Furthermore, the simple open-tubular capillary design has lead itself to a variety of automation, injection and detection strategies developed previously for more conventional analytical technologies.

The general instrumental set-up involves a capillary filled with an electrolyte solution and a high voltage power supply connected to electrodes in contact with small fluid filled reservoirs at either end of the capillary. The power supply is operated in order to apply an electric potential field tangential to the capillary surface, in the range of 100–1000 V/cm. When the potential is applied, migration processes occur. The electric field imposes a force onto charged species leading to the electrophoretic migration of sample molecules within the capillary. Furthermore, when file capillary surface is charged, a flow of the whole solution is induced by electro-osmosis. Therefore, electrophoresis is in most cases superimposed on a so-called electroosmotic flow (EOF). Species moving in the capillary as a result of these forces will then be transported past a suitable detector, absorbance and fluorescence being the most common. Capillary electrophoresis has been applied to numerous analytes spanning pharmaceutical, environmental and agricultural interests. A common focus amongst these activities is bioanalysis. Separation methods are developed for peptide sequencing, amino acids, isoelectric point determination for proteins, enzyme activity, nucleic acid hybridization, drugs and metabolites in biological matrices and affinity techniques such as immunoassays. Furthermore, buffer additives such as cyclodextrins and micellar phases have added the ability to perform chiral separations of biologically active enantiomers of tryptophan derivatives, ergot alkaloids, epinephrines and others which is of great interest to the pharmaceutical industry.

The capillaries described above generally have internal diameters between 50–200 µm and are formed in fused silica. The microfabrication of capillaries has also been accomplished by machining directly onto planar, silicon-based substrates. Silicon substrates have an abundance of charged silanol groups and thus generate considerable EOF. In the case of micromachining, EOF can be an advantage in that the flow of the bulk solution can be used for many liquid handling operations. There has recently been intense activity in the area of chemical instrumentation miniaturization. Efforts have been made to reduce whole laboratory systems on to microchip substrates, and these systems have been termed micro-Total Analytical Systems (µ-TAS). As already mentioned, most of such µ-TAS devices to date have been produced photolithographicly on silicon-based substrates. This process involves the generation of the desired pattern on a mask, through which a photoresist coated silicon dioxide wafer is exposed to light. Solubilised photoresist is then removed and the resulting pattern anisotropically etched with hydrofluoric acid. Etched capillaries are then generally sealed by thermal bonding with a glass covert The bonding technique in particular is labour and technology intensive and thermal bonding requires temperatures between 600–1000° C. This bonding technique has a very low tolerance of defect or presence of dust and requires clean room conditions for the fabrication, which means that the production is very expensive. Alternative fabrication techniques have also been developed based on organic polymers. Fabrication of polymer microfluidic devices has been shown by injection moulding or polymerising polydimethyl siloxane (PDMS) on a mould. These two techniques have the advantage to replicate a large number of micro-structures with the same pattern given by the mould. Other techniques based on electromagnetic radiation either for polymerisation under X-ray (LIGA) or for ablation have also been recently shown to be feasible. This last fabrication technique allows fast prototyping by writing pattern on a substrate that can be moved in the X and Y directions. Different structures can then be fabricated just by moving the substrate in front of the laser beam.

As already mentioned, electroosmotic pumping is used here not only to separate samples but also to dispense discrete amounts of reactants or to put in contact solutions for the reaction in continuous flow systems. A large diversity of structures and electrical connections have been presented which permit to deliver and analyse samples in less than a millisecond by electrophoresis for example.

This spectacular property also evidences that, in these microchannels, the main transport mechanism between two flowing solutions is diffusion. As different species exhibit different diffusion coefficients, efficient mixing becomes problematic, and this is often presented as a serious limitation for the wider use of microfluidic in total analysis systems. In order to solve this problem, mixers have been presented, where the flows are for instance divided in smaller channels (20 μm) before being placed in contact. In this manner, the diffusion time is reduced and hence the mixing efficiency enhanced.

Many recent advances in chemical analysis have involved the incorporation of biomolecules capable of selective and high affinity binding to analytes of interest Such devices are often termed biosensors, which involve real-time transduction of the binding event into an electronic signal, but also include analytical technology consisting of immunoassays, enzyme reaction, as well as nucleic acid hybridisation. Bio-analytical devices utilising this technology have been applied to a wide range of applications in medicine agriculture, industrial hygiene, and environmental protection. Enzyme electrodes represent the oldest group of biosensors and are being increasingly used for clinical testing of metabolites such us glucose, lactate, urea, creatinine or bilirubin. Several groups have developed needle-type electrodes. for subcutaneous glucose measurements. A microelectrochemical enzyme transistor has been developed for measuring low concentrations of glucose. Efforts continued towards other clinically relevant metabolites particularly for the multiple-analyte determination. Strategy to incorporate affinity steps is also an active area of biosensors. The emerging area of DNA hybridisation biosensors has been a very popular topic for the clinical diagnosis of inherited diseases and for the rapid detection of infectious microorganisms.

Recent interest in the development of miniaturised, array-based multianalyte binding assay methods suggests that the ligand assay field is on the brink of a technological revolution. The studies in this area have centered largely on antibody or DNA spot arrays localised on microchips which are potentially capable of determining the amounts of hundreds of different analytes in a small sample (such as a single drop blood). Array-based immunoassay methods shows the particular importance in areas such as environmental monitoring where the concentrations of many different analytes in test samples are required to be simultaneously determined. Affymetrix developed ways to synthesise and assay biological molecules in a highly dense parallel formal Integration of two key technologies forms the cornerstone of the method.

The first technology, light-directed combinatorial chemistry, enables the synthesis of hundreds of thousands of discrete compounds at high resolution and precise locations on a substrate. The second laser confocal fluorescence scanning permits measurement of molecular interactions on the array.

Recently, the Laboratoire d'Electrochimie of the EPFL Lausanne has presented a patterning technique based on the photoablation process. In order to fabricate microarrays of proteins, the polymer substrate is firstly blocked with a bovine serum albumin (BSA) layer avoiding non specific adsorption of protein on the substrate layer. Microspots are then created on the surface by photoablation of the BSA layer, on which avidin can be adsorbed yet. This micropatterning technique allows then to specifically adsorb antibodies linked to biotin on the avidin spots as visualised by biotin-fluorescein complex.

Apart from electrophoretic separations and hybridisation, an increasing number of applications on μ-TAS have been shown in the last few years. Full DNA analysers have been implemented in a single device with a polymerase chain reaction (PCR) chamber followed by an electrophoretic separation. Continuous flow PCR has also been shown where the analyte solution is driven through capillary crossing zones of different temperatures. Other genetic analysis have also been demonstrated comprising high speed DNA sequencing, high density parallel separation or single DNA molecule detection. Another application of μ-TAS has been shown in electrochromatography. An open-channel electrochromatography in combination with solvent programming has been demonstrated using a microchip device. Others have successfully used μ-TAS to conduct immunoassays involving competitive markers, noting several advantages over more traditional formats including (a) high efficiency separations between competitive markers and antibody-marker complexes, (b) excellent detection limits (0.3–0.4 amol injected) at high speed, and (c) good potential for automation. This has first been demonstrated in a micromachined capillary electrophoresis device by Koutny et al. Cortisol was determined in serum using a competitive immunoassay that was subsequently quantitated using μ-TAS. A microfluidic system was fabricated on a glass chip to study immobilization of biological cells on-chip. Electroosmotic and/or electrophoretic pumping were used to drive the cell transport within a network of capillary channels. An automated enzyme assay was performed within a microfabricated channel network. Precise concentrations of substrate, enzyme and inhibitor were mixed in nanoliter volumes using electrokinetic flow. Finally, the new insight in the use microfabricated system has been to combine the advantage of parallel reactions and liquid handling in extremely small volumes with an electrospray or nanospray interface for mass spectrometry analysis. This last application opens a way to efficiently use the microchip format not only for genetic analysis where it is already recognised but also in protein sequencing.

Several microfabrication processes have been shown that modify the surface properties of the polymer.

It is known that reactions of gas plasmas with polymers can be classified as follows:

1. Surface reactions:
   Reactions between the gas-phase species and surface species produce functional groups and/or crosslinking sites at the surface.
2. Plasma polymerisation:
   The formation of a thin film on the surface of a polymer via polymerisation of an organic monomer such as $CH_4$, $C_2H_6$, $C_2F_4$ and $C_3F_6$ in a plasma.

3. Cleaning and etching:
   Materials are removed from a polymer surface by chemical reactions and physical etching at the surface to form volatile product.
   Patent of particular relevance in the etching process:
   U.S. Pat. No. 5,099,299 (Dyconex)
   Patent with particular relevance in lamination sealing of polymer micro-structure:
   WO 991197 17 (Aclara Biosciences)
   Patent of particular relevance in patterning of properties:
   WO 9823957 A(EPFL)
   Other patents on microfabrication and fluidic control by surface properties:
   WO 9823957 A(EPFL)
   WO 9846439 (Caliper technology)
   WO 9807019 (Gamera Bioscience)

SUMMARY OF THE INVENTION

According to the present invention, an etching method for manufacturing micro-structures or openings in a multilayer body made of selected materials is provided, wherein the surface properties of the layers are controlled individually and preferably simultaneously control, so that conduits, grooves, reservoirs, holes and so forth are formed and exhibit various surface properties allowing further functionalisation of selected surfaces as well as fluid handling.

Further, an etching method of the above kind is provided where the conduits and reservoirs are manufactured in sequential etching steps between which selected layers can be removed or added to the multilayer body or between which the properties of selected etched surfaces can be modified.

Still further, such an etching method is provided for manufacturing micro-structures or openings in a multilayer body which can contain a selected sequence of insulating and optically or electrically conductive layers, whereby measurement and/or detection of one or more analytes and/or fluid handling means are provided.

Also, such an etching method is provided where a plurality of layers is manufactured simultaneously or where various etching processes are used.

Thus, the present invention provides a fabrication method for the three dimensional structuration and patterning of at least two different surface properties for micro-systems.

The invention further comprises products manufactured using this method as defined in the claims.

The technology is based on the plasma etching of organic polymer sheets partially protected by a metallic mask. The originality of the process is to pattern the surface properties by the same physical means as the one used for the three dimensional fabrication and simultaneously to this fabrication. Surface properties mean, but are not limited to hydrophobicity hydrophilicity, conductivity, reflectability, rugosity and more precisely the chemical and/or physical state of the surface. It is also possible to generate the desired fonctionalities, for instance carboxylic acid, ester, ether, amid or imide, during the etching process. The patterning of the different properties may be achieved by two different techniques that may be used separately or simultaneously.

1. The fabrication of multilayers of polymer of different properties, for example, a sandwich composed of two thin layers of electrical insulator (polystyrene) spin coated on both sides of a conducting polymer sheet (carbon filled polystyrene). Plasma etching cuts the three layers vertically, thereby providing a band of conducting material isolated by the two insulating layers.

2. The substrate partially protected by a mask on both sides is placed in the middle of two chambers (A and B), separated hermetically, inside which a plasma is generated differently in chamber A than in chamber B. For this, the surface exposed to chamber A is treated with an oxidative plasma ($O_2$) while the other one with a non-oxidative plasma ($N_2$) The surface of such a hole would be half hydrophilic and half hydrophobic with respect to the etching rate of both plasma.

In a preferred embodiment, the technology may be applied to manufacture micro-analytical systems that are devoted to many applications, like for instance chemical and biological analysis, synthesis and/or separation. Furthermore, in another embodiment, the technology may serve to manufacture devices devoted to reactions occurring at the interface between a liquid and a solid surface or at the interface between two solutions.

For example, microelectrodes or micro-needles may be fabricated and used for electrochemical detection or in mass spectrometry sampling. The system may be used for liquid extraction between two phases like partitioning experiments. Furthermore, the technology may be applied to every kind of induced flow like diffusion, convection (for example by electroosmosis) or migration (for example by electrophoresis). The technology may also be used for applications where the plasma created surface is chemically or biochemically derivated in order to perform chemical or biochemical assays. As further example, the technology may be applied to reaction types where the temperature may be adjusted and/or controlled for instance by the use of electrical means like integrated thermistors or thermocouples, as for example for PCR reactions.

DESCRIPTION OF THE PREFERRED EMBODIMENTS

Figure 1A:
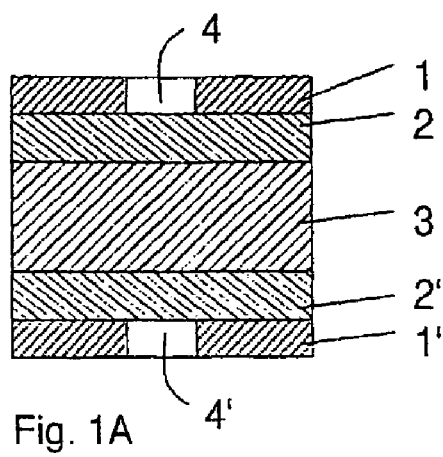
FIGS. 1A–1E show schematic sectional views through a portion of an embodiment of the multilayer body showing methods for manufacturing micro-structures or openings in this multilayer body which is coated on both sides and which is made of a plurality of materials.

The term "micro-structure", as used herein, means and refers to a single micro-channel, an array of micro-channels or a network of interconnected micro-channels not limited in shape but having a cross-section enabling micro-fluidic manipulations. In accordance to the present invention, these "micro-structures" are usually formed in e.g. a plate, a planar substrate or the like, and they are usually made in at least two layers, one containing the desired micro-structure pattern and a second one serving as sealing component.

The term "openings", as used herein, means and refers to hollow passages or spaces. These openings include for example reaction chambers, reservoirs, wells and the like. They can stand alone or can be positioned at either end of a channel. When such openings stand alone, they can for instance be used for reagent introduction, mixing, incubation, washing, reaction, detection and the like, as required in e.g. homogeneous assays. When connected to a channel, they are for instance used as means for introducing a fluid into a main channel or a channel network. When going through a plurality of layers, these openings can also be used to form a micro-structure having selected portions of various surface properties.

In the present invention, "channels" and "micro-channels" are conduits or means of communication (e.g. fluid communication) between openings and the like. They include for instance trenches, grooves, flumes, capillaries and so forth, without limitation in shape. The "micro-channels" are yet limited to 0.1–1000 µm in at least one of their dimensions.

The "surface properties", as this term is used herein, mean and refer to the chemical and/or physical state of the surface. They for instance include hydrophobicity, hydrophilicity, conductivity, reflectability, rugosity, sieving, affinity and so forth. The term "conductivity" refers here to the ability of a surface to transfer electrons from another material or solution into its bulk or, in the opposite, to transfer electrons from its bulk to another material or solution in contact Those surface properties are intrinsically related to the nature of the materials used to form each layer, and, in accordance with the present invention, they can be modified in some parts of a multilayer body during the structuration process. In some embodiments, the surface properties of selected parts of a multilayer body can be further modified after the structuration process. The surface properties for instance serve to control the displacement or not of a medium within the formed micro-structures or openings. In accordance with the present invention, the surface properties can be selected in various parts of a multilayer body in order to, for instance, prevent or favour capillary flow, electroflow (i.e. electrokinetic flow, electroosmotic flow, electrophoretic flow, dielectrophoretic flow and so forth) chromatographic retention, molecule binding (e.g. adsorption or physisorption), optical or electrical conductivity, and so forth.

FIGS. 1 to 4 show different manners of manufacturing micro-structures in a multilayer body with simultaneous control of the properties of the etched surfaces. In some embodiments, the multilayer body is a plastic film having an etch resist coated on one or both sides. The term "etch resist" refers herein to a substance which is resistant to the etching medium or, at least, is much more resistant than the material to be etched.

In a preferred embodiment, plasma etching, i.e. a technique in which the etching medium is gaseous, is used preferably to other techniques such as wet chemical etching or photoablation due to the difficulty of the former to provide the necessary precision required to manufacture micro-structures and due to relatively low processing speed of the latter. It is yet possible to use combinations of these methods in order to further modify selected surfaces of etched layers in order to modify their functionality.

The precision of the plasma etching method directly depends upon the precision of the pattern structured in the etch resist coatings and upon the thickness of the layer to be etched. Any available methods like, for instance, the photochemical processes used in the electronics industry can be used to structure the etch resist like, for instance, a photoresist with micrometer precision. Plasma etching has the further advantage to allow for a directional etching (anisotropic plasma. etching), which prevents lateral etching of material below the etch resist, a phenomenon called "underetching". Furthermore, the etch resist can be removed after micro-structure or openings fabrication when the material of the etch resist is not desired. This is for instance the case of plastic films that have been metallised e.g. by vacuum metal deposition before the etching process, but that cannot be constituted of a metal for their applications. Finally, the main advantage of plasma etching with respect to the present invention is that the etching medium can be varied in order to pattern the desired surface property of selected materials.

FIGS. 1 to 4 show different manners of micro-structuring polymer layers providing various surface properties to the etched surface of each material composing the multilayer body. The figures are not to scale and represent only a portion of the entire bodies. They also present different stages of an etching process taking place from both sides of the multilayer body, even though each side of the multilayer body can be processed sequentially.

FIG. 1A shows a portion of a multilayer body for instance made of a plastic film 3 sealed on both sides with a laminate 2, 2' made of a second material that is coated by an etch resist 1, 1'. The central plastic film is, for example, 100 μm thick polyethylene terephthalate (PET), whereas the laminate film is 25 μm thick polyethylene (PE) sealed to the first layer by any available technique. The etch resist can be a metal such as copper with a thickness of 12 μm which has been applied by a known electrolytic process, by laminating, by sputtering or any other available technique. This etch resist already contains recesses such as 4 and 4' that have the shape necessary to manufacture the desired pattern, and that are located at the desired positions where openings are to be formed. The preliminary steps of photoresist application on both sides of the body and further development of this photoresist coating to obtain the recesses 4 and 4' of the desired pattern are not presented in any of the below figures, their fabrication being not an object of the present invention.

Figure 1B:
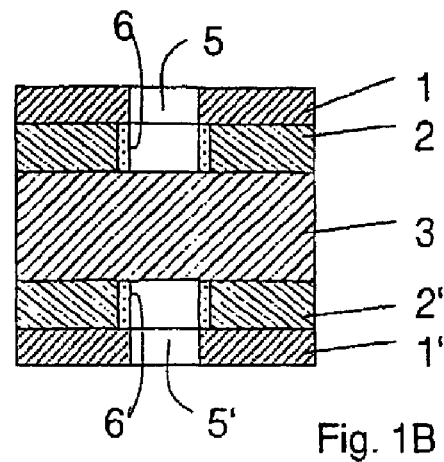
Figure 1C:
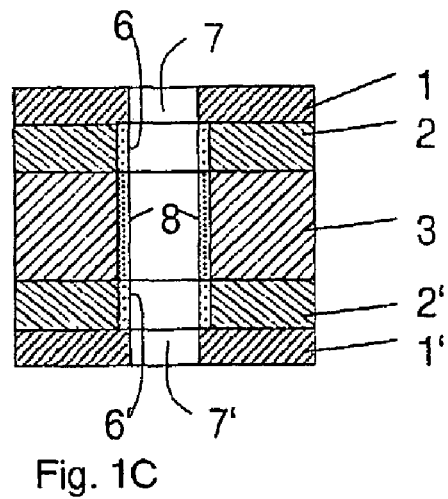
Figure 1D:
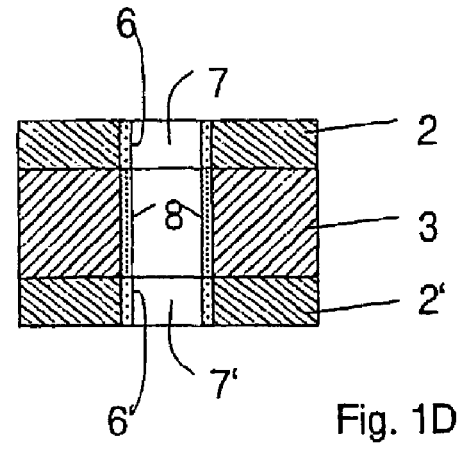

In FIGS. 1B and 1C, openings 5, 5' and 7, 7' are etched successively through the layers 2, 2' and, respectively, 3, thereby resulting in passages exhibiting different surface properties 6, 6' and 8. In FIG. 1D, the etch resist 1 is removed by any available method, as may be required for various applications. Similarly, the etch resist can be coated with another layer (not shown) for instance for interfacial connections of the metal coatings. Any of these etching steps can be preceeded by a treatment in a solution, not shown, for reducing the etching time. Furthermore, any of these etching steps can be followed by a treatment in order to modify the surface properties of the structured openings. In the example where the body is a PET film sealed to a copper coated laminate PE film, the surface of the PET film is made highly hydrophilic during an oxidative etching process (as with oxygen plasma etching), whereas the surface of the PE remains much less hydrophilic. In this case, a drop of aqueous solution deposited on the copper coating 1 will not be able to enter the opening 7 by capillary fill. An external force must be applied to this drop to let it reach the hydrophilic surface 8. Once the Surface 8 is in contact with the drop, capillary fill is induced in this portion of the micro-structure, but it is stopped as soon as the solution front reaches the second hydrophobic surface 6'. Here again, an external force is necessary to let the fluid front penetrate into the opening 7'. This example illustrates one manner of handling fluids in micro-structures formed according to the present invention. Etching providing surfaces of medium hydrophobicity can also be used to slow down the fluid flux in a given portion of a micro-structure, which can be advantageous to complete a reaction, an adsorption and so forth in the case where longer times are needed.

Figure 1E:
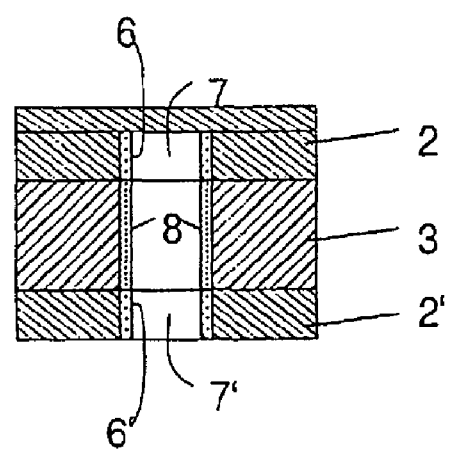
Figure 2A:
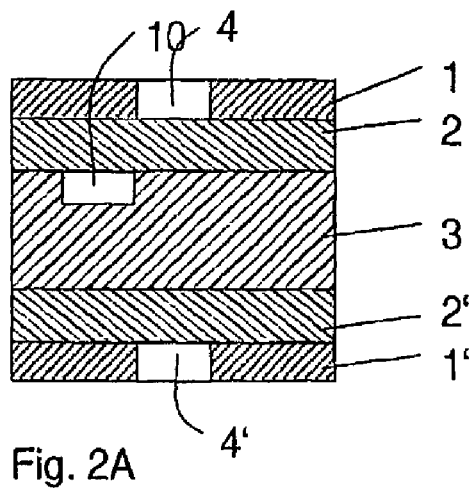
FIGS. 2A–2E show schematic sectional views, through a portion of an embodiment of the multilayer body showing methods for manufacturing micro-structures or openings in this multilayer body which is coated on both sides and which is made of a plurality of materials, one of the layers already containing micro-structures or openings.
Figure 2B:
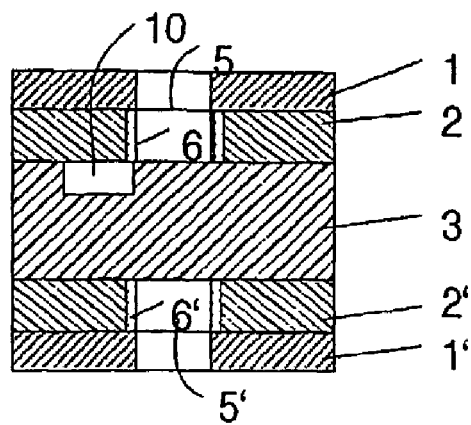
Figure 2C:
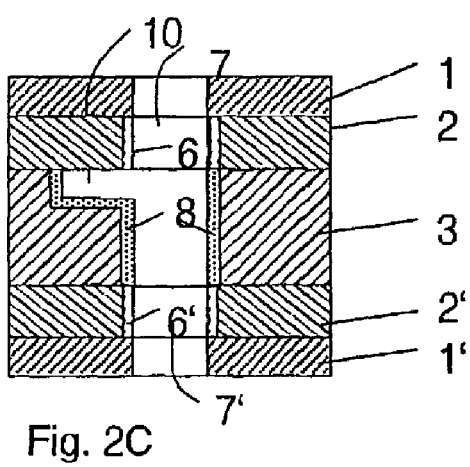
Figure 2D:
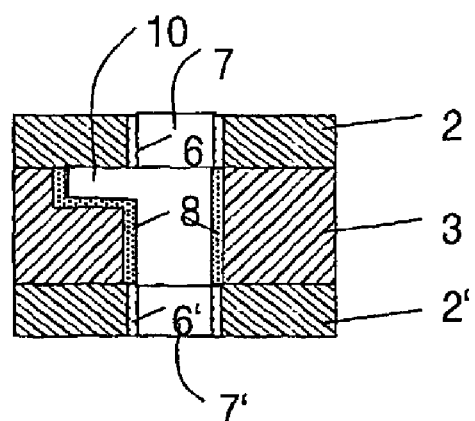
Figure 2E:
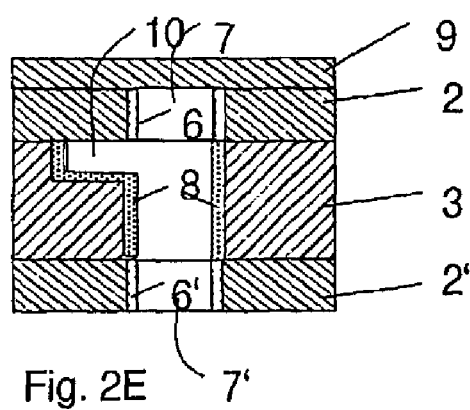

In FIG. 1E, the structured multilayer body is coated by a supplementary layer 9 using any conventional method, such as for instance lamination, in order to seal one end of the formed structure, thereby providing a micro-structure with an opening only at the opposite end.

Figure 3A:
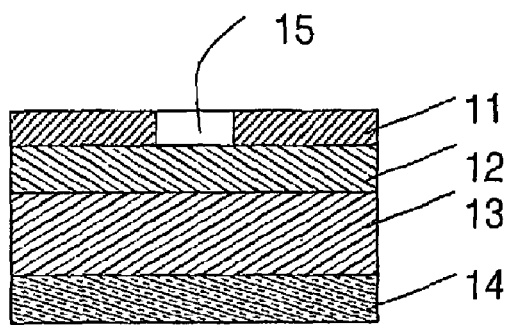
FIGS. 3A–3C show schematic sectional views through a portion of an embodiment of the multilayer body showing methods for manufacturing micro-structures or openings in this multilayer body made of a plurality of materials using a plurality of etching processes allowing to process one layer and to remove another one simultaneously.
Figure 3B:
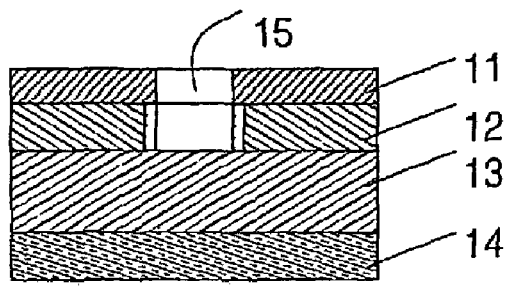
Figure 3C:
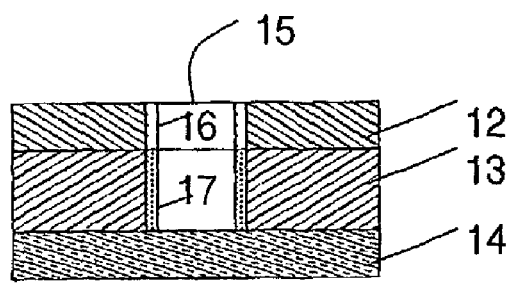
Figure 4A:
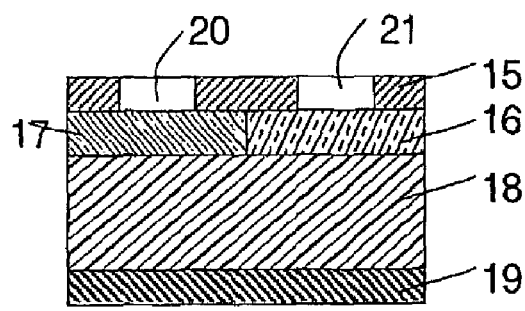
FIGS. 4A–4C show schematic sectional views through a portion of an embodiment of the multilayer body flowing methods for manufacturing micro-structures or openings in a multilayer body made of a plurality of materials, using a plurality of etching processes allowing to discriminate the structuration of two different portions of a layer.
Figure 4B:
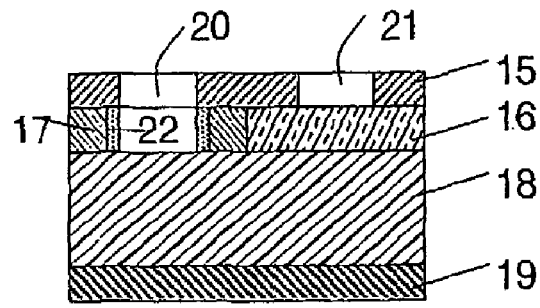
Figure 4C:
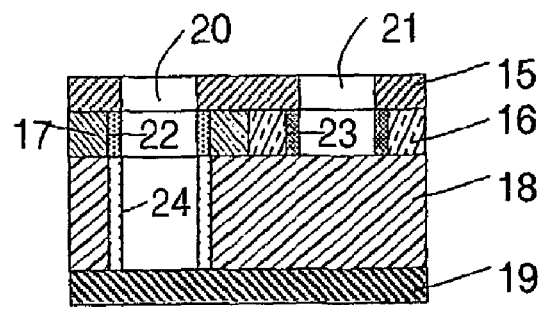

FIG. 2 shows different stages of a fabrication process totally similar to that clarified for FIG. 1. The only difference consists in the fact that the central layer 3 contains one or more micro-structures or openings 10 located at the desired position(s) either to prevent (not shown) or to allow connection with the opening to be etched. In this last case, the shape of the complete micro-structure formed by the etching process is modified, as well as the extent of the surface properties 8 patterned during this etching process. In another variation, the micro-structure(s) or opening(s) 10 is (are) made of a third material such as e.g. a polymer, a gel, a paste and so forth or is (are) filled with an assembly of materials such as fibers, waveguides, beads and so forth FIGS. 3 and 4 show two different ways of fabricating micro-structures in different layers using a plurality of etching processes. In FIG. 3, layer 11 is resistant to a first etching process and contains the recess 15 to produce the desired pattern in layer 12. A second etching process is then used to fabricate the desired micro-structures or openings to simultaneously remove material in layer 13, without affecting the surface properties 16 of the previously etched layer and creating different surface properties 17 in layer 13. In the present case, the layer 11 only serves as an etch resist for the first fabrication step, because it is not desired for the use of the structured body. If this layer is prejudicial to the second etching process, it can be removed before structuring layer 13. In another embodiment, layer 11 can be selected in such a manner that it is resistant to the first etching process, but not to the second, so that both layers 11 and the desired pattern in layer 13 are etched simultaneously. In FIG. 3, the etched micro-structures or openings do not extend through layer 14 which is resistant to both etching processes. However, this is not a necessity of the process, and the multi layer body can be selected in such a manner that both sides can be etched simultaneously following the above procedure. Furthermore, the above operations can also be repeated several times in order to fabricate micro-structures and openings in a body containing a larger number of layers.

FIG. 4 shows a method similar to that presented in FIG. 3 for the structuring a multilayer body and the patterning of surface properties of various natures in different layers. The etch resist 15 contains a plurality of recesses 20 and 21, and the second layer is made of a plurality of materials (two materials 16 and 17 in the case shown). None of the etching processes is able to attack the etch resist 15, and this layer is not removed between two fabrication steps. Materials 16 and 17 are selected in such a manner that only material 16 is resistant to the first etching process, so that a recess is created in layer 17 only. In a second step, a second etching process is used to produce the desired micro-structures of openings either in layer 16 only, either in layer 18 only (cases not shown) or in both layers 16 and 18 simultaneously. This leads to a three dimensional structure where holes 20 and 21 have different surface properties depending on the nature of the layers and on the step during which they are etched. In the present example, surfaces 22, 23 and 24 can have different properties or, if layers 16 and 18 are of made of similar materials, surfaces 23 and 24 have the same properties whereas 22 is different.

It must also be stressed that the surfaces of the etched micro-structures described in any of FIGS. 1 to 4 can be further treated to bind, immobilise or coat a molecule in selected materials and/or selected layers. This can for instance be applied to immobilise biological molecules on a portion of a layer in order to perform a separation or an assay. Affinity chromatography, enzyme linked immunosorbent assays, receptor binding assays are some examples of the applications of the micro-structures manufactured according to the invention. Similarly organic material as for instance lysine, polyacrylamide or sodium dodecyl sulfate can be attached to selected etched layers in order to perform electrophoresis.

Figure 5:
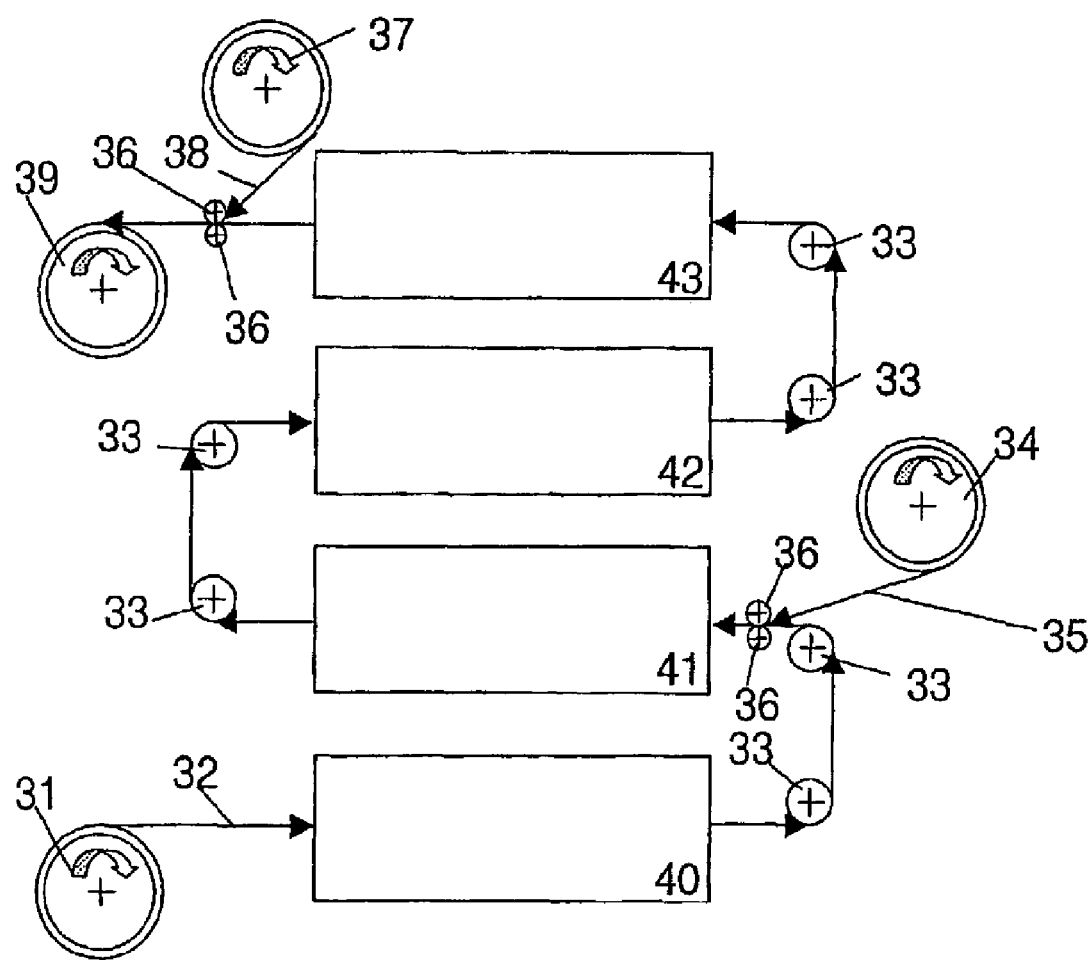
FIG. 5 is a schematic diagram showing a method for processing a plastic film of indeterminate length in accordance with the present invention, FIGS. 6A–6E schematically show a sequence of microfabrication with plasma etching.

FIG. 5 shows a continuous process for producing micro-structures and openings in plastic films. A supply roll 31 supports the multilayer body 32 that can be either coated with an etch resist on one or both sides containing preformed recesses or not. Small rolls 33 direct the multilayer body through various process stages and steps 40 to 43, and the final end of the multilayer body is wound up on a take-up roll 39 to collect the final product. This step-up can for instance be used to process the structure shown in FIG. 4. A first stage 40 comprises all the steps required to coat the multilayer body 32 with an etch resist 15 containing recesses 20 and 21. In a metal etching stage 41, etching of metal coatings 15 takes place at the location of recess 20 where the microstructures and/or openings are to be formed. In the next process stage 42, another second process is used to etch layers 16 and 18 simultaneously, thereby creating the desired surface properties 22, 23 and 24 in each material. During the last process stage 43, the etch resist 15 is removed, and the structured multilayer body is finally sealed by laminating a supplementary plastic film 38, yielding the final product 39.

Further process stages can also be added to the strip installation, and the various process stages can be devoted to other functions like washing, curing, coating, surface modification, immobilisation, and so forth. Similarly, layers can be added to the body between two or several process stages. This is illustrated in FIG. 5 by the supplementary roll 34 that allows to laminate a plastic film 35 that is for instance used as a sealing of the etched micro-structures and openings formed in previous process stages and/or as a supplementary etch resist for the next process stages.

In the following, an example of an experiment carried out using the method according to the invention and its results are described in order to exemplify the concept of the invention.

For the experiment, polyimide foils coated on both sides with 5 µm thick copper are used as substrate material.

In a first step, plasma etched micro-structures are fabricated. Plasma is a highly excited state of matter, typically that of a diluted gas, in which a certain percentage of the gas atoms and molecules are ionised and then split to form highly reactive gas radicals. These chemically aggressive particles react preferentially with organic materials and generate reaction by-products which are subsequently desorbed from the surface. If the surface of an organic dielectric is partially covered with a metal mask, only the open areas can be attacked.

40×40 cm$^2$ polyimide foils of 50 µm thickness and coated on both side with 5 µm copper are fixed in a frame. The copper is chemically etched after patterning of photoresist with the help of a computer printer, e.g. a 25'000 dpi high resolution printer.

Figure 6:
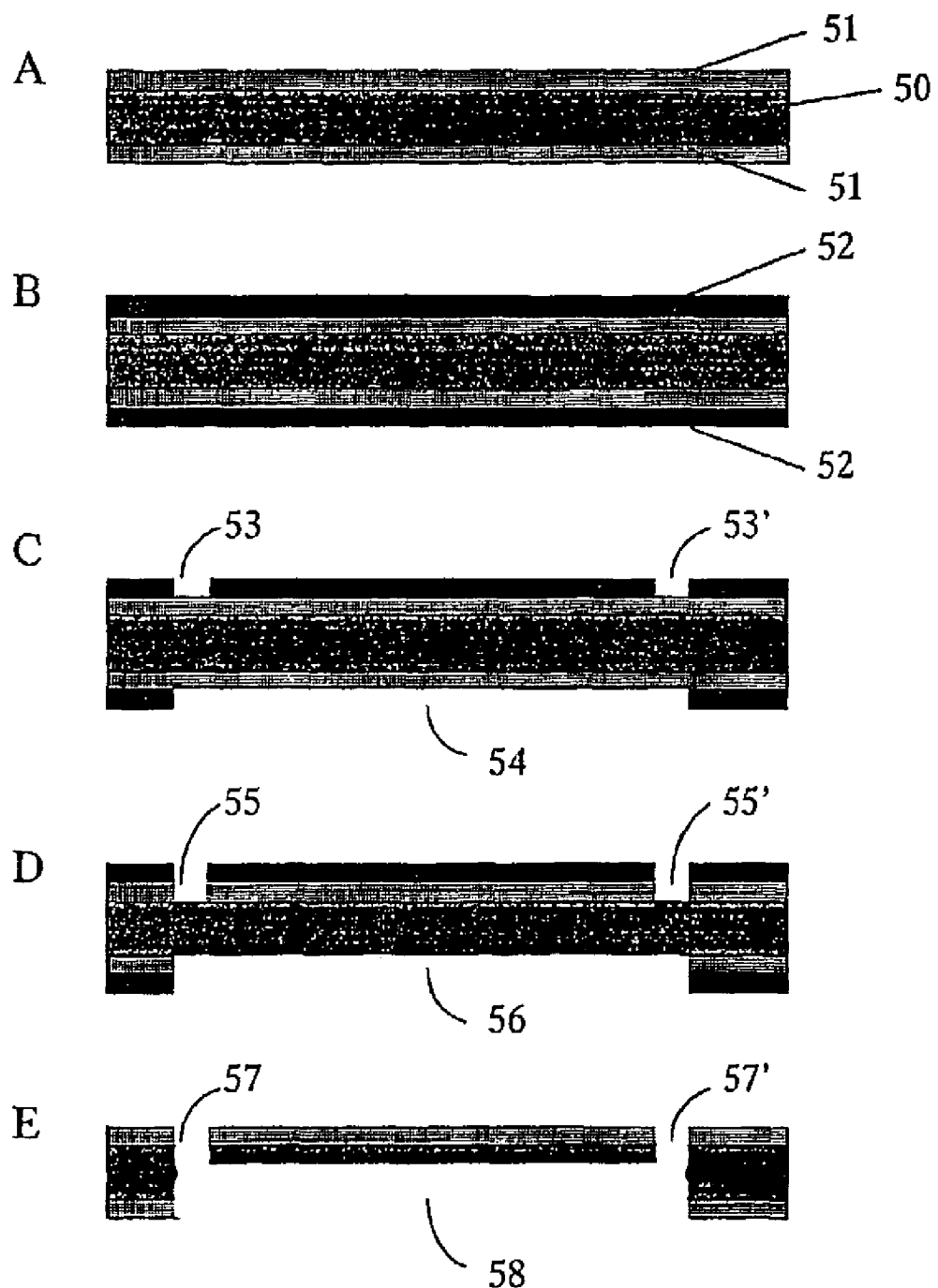

In FIGS. 6A–6E, the manufacturing sequence for a double-sided foil with plasma-drilled micro-structures is shown schematically. FIG. 6A shows a foil 50 coated on both sides by a copper layer 51. In FIG. 6B, these copper layers are then covered by a photoresist 52 which is further exposed to light in such a manner that two holes 53 and 53' and one recess 54 are created, as shown in FIG. 6C. This multilayer body is then etched chemically in order to structure the copper layers and create holes 55 and 55' and recess 56 of the same patterns as those made within the photoresist layers (FIG. 6D). The polymer foil is then structured by exposition to plasma in order to create an inlet 57 and an outlet 57' reservoir on one side and a groove 58 on the other side (FIG. 6E).

Due to the fact that plasma has access to the substrate from both sides, the holes 57 and 57' and the groove 58 are formed simultaneously when the copper 51 has been patterned on both sides of the foil 50. After this process, the surface state of the polymer can be very hydrophobic or hydrophilic depending on the plasma composition that is either O2, CF4 or N2. In the below examples, oxygen plasma has been used in order to get an oxidised surface that can generate capillary flow inside the microchannels. Nevertheless, the surface outside of the capillary, protected by the copper layer will remain hydrophobic.

The above process can be repeated in order to create structured portions of different level (various depths), thereby producing recesses, cavities, protruding features and the like. This can for instance be used to create contact among the various layers constituting the multilayer body.

In another example, this process is used to integrate electrodes within the device. To achieve this, well-defined portions of the structured device (as for instance portions of the groove 58 shown in FIG. 6E) are exposed again to the plasma through a novel copper mask containing the desired patterns. In this manner, the polymer foil 50 can be further etched until the copper layer 51 is reached. After these steps, a metal such as for instance gold is electroplated on the copper layer in order to get a surface which is suitable for electrochemistry purposes.

Figure 7:
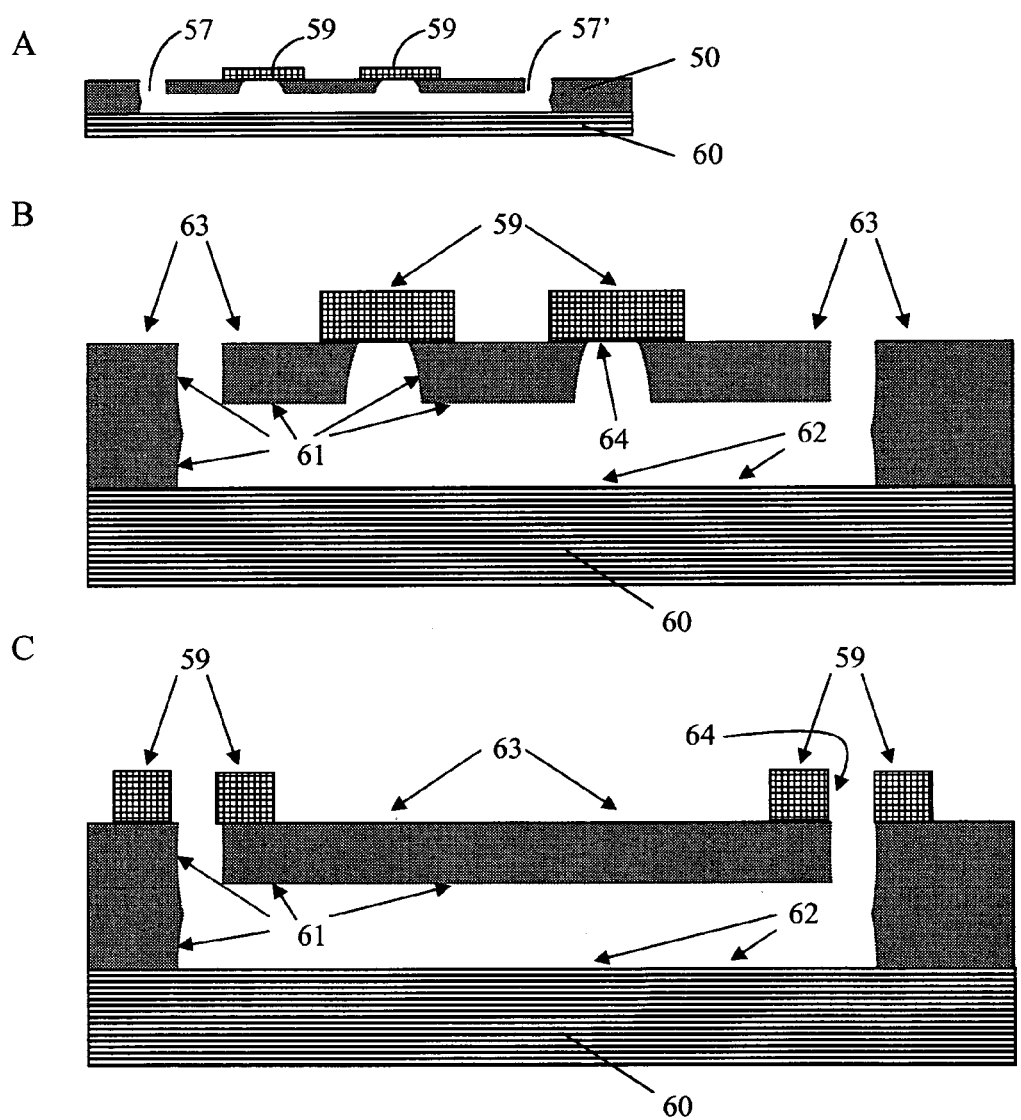
FIGS. 7A–7C show a side view of micro-structures fabricated by plasma etching with the electrodes and the lamination.

An example of such a plasma etched device is shown in FIG. 7A. In the present case, the device is produced in a 50 µm thick polyimide foil 50, and it contains: one microchannel with one inlet 57 and one outlet 57', as well as two micro-electrodes 59 that are gold coated copper pads. The final structure is then sealed by lamination of a 35 µm thick polyethyleneterephthalate-polyethylene (PET-PE) layer 60 (Morane LTD, UK) with the same procedure as the one already presented elsewhere.

It is very important to observe the surface properties of the channel after the fabrication process, which is schematically described in FIG. 7B. Indeed, inside the microchannel, the surface 61 is charged and hence hydrophilic, which is necessary to enable capillary and/or electroosmotic flow. The wall 62 of the sealed micro-channel made of the laminated layer 60 is yet less hydrophilic due to the nature of PE. Outside of the capillary, the surface 63 must be hydrophobic, so as to avoid the dispersion of the drop of solution around the openings serving as inlet and outlet. In the below examples, polyimide, which is an hydrophobic material is chosen for that purpose, since it becomes hydrophilic upon exposition to the oxygen plasma. Another surface property is the conductivity of the surface 64 where the metallic layer is in contact with the solution. These structures therefore demonstrate the concept of the invention: patterning different surface properties that are needed for controlling of the fluid flows, performing chemical reactions, detecting analytes and so forth.

FIG. 7C shows another example of distribution of the above surface properties, where electrodes are placed directly above the inlet and outlet of a sealed micro-channel.

Next, the electrochemical detection is performed by cyclic voltammetry with an AEW2 portable potentiostat (Sycopel Scientific, UK) by connecting one of the electrodes as working electrode (WE) and another one as counter electrode (CE). A freshly oxidised Ag|AgCl wire is used as reference electrode and placed on the top of one channel entrance in contact with the solution to be analysed. Cyclic voltammetry characterisation of ferrocene carboxylic acid is first presented to understand the behaviour of the gold coated microelectrodes similarly to what was presented earlier in a previous paper.

Now, micro-structures fabricated according to the present invention are then used to demonstrate some examples of analytical applications, namely immunological assays and enzymatic reactions.

For the example of immunoassay, the immobilisation of the mouse antibodies was performed by physisorption at pH 7 during one hour at room temperature. Depending on the experiments, between 1 and 100 µg/ml of antibody concentration is used. The surface is then blocked with 5% Bovine Serum Albumin (BSA). The immunoreaction is performed by filling dried channels containing immobilised mouse antibody with a goat antimouse-HRP conjugate and incubating it 5 minutes at dilutions between 1/225'000 and 1/25'000 titre. After the incubation with the conjugate, the substrate solution containing 100 mM Hydroquinone and 100 mM peroxide is added to the channel to allow the electrochemical detection of Horse-Raddish-Peroxidase (HRP) with a similar procedure as that proposed by Wang et al. Between each step, a washing procedure is performed with a solution of washing buffer at pH 7.4 and containing 0.1 M phosphate buffer and 0.1% BSA.

In a second example, the use of the microchip is demonstrated for an enzymatic assay. Plasma etched micro-structures have been used here for the detection of glucose. A solution of Glucose oxidase (enzyme) and ferrocene carboxylic acid (mediator) is mixed with a solution of glucose and filled in the microchannel where a cyclic voltammetric detection is performed.

In another schema, the Glucose oxidase and ferrocene solution is filled into the micro-channel, and the glucose solution is placed on one of the reservoirs.

In a further example, 2 µL of glucose oxidase and ferrocene carboxylic acid is deposited and let dried on the electrode pads outside of the channel. Then a solution of glucose is deposited on the dried solution and a cyclic voltammetry is performed.

In the following, the obtained results are shortly described.

First, the aspect of the structures used is addressed. Microscopy examination of the plasma etched plastic foils 70 before sealing by lamination of a PET-PE layer shows the different patterns that compose the micro-structure. Four top views of the device are presented in FIG. 8, which contains a yellow-brown colour due to the light absorption of the polyimide layer 70. In the upper view on the left, the presence of the micro-channel 71 is shown as a hell pattern in the middle of the image, meaning that the thickness of polyimide at this place is smaller. At both ends of the channel, there is a hole 72 that serves as reservoir or as inlet and outlet, thereby allowing to access the liquid inside the channel after the lamination procedure. The other lines patterned on the surface 73 are the gold coated pads to connect the electrodes with the potentiostat. In the closer views of the device presented in FIG. 8, it can been observed that the geometry of the electrode is a disk that is slightly recessed from the channel level.

Figure 8:
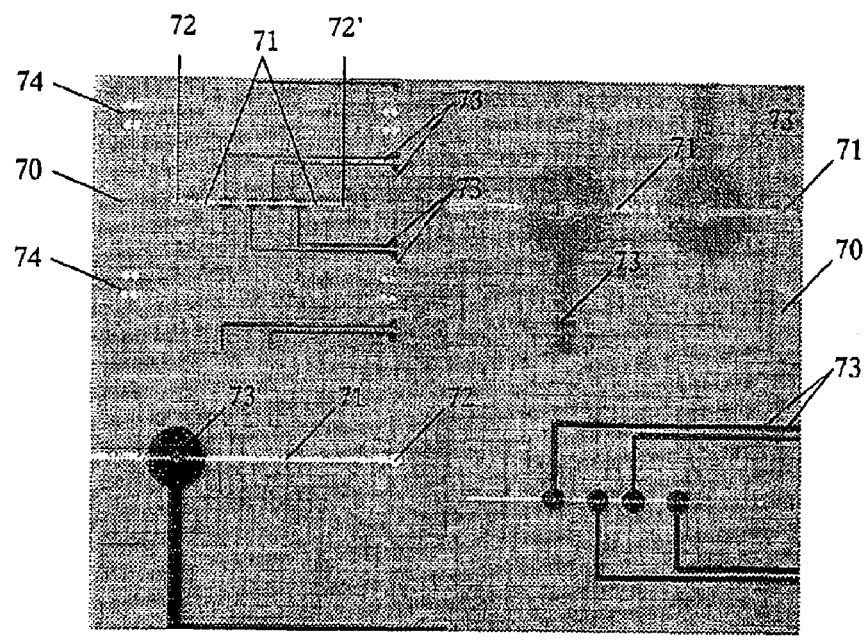
FIG. 8 is a top view of the unsealed micro-structure, together with closer views of the electrode microdisk inserted in the microchannel.

It is worth noting that the upper view on the left side of FIG. 8 also shows series of four holes 74 that are used for the precise alignment of the device during its fabrication process.

Figure 9A:
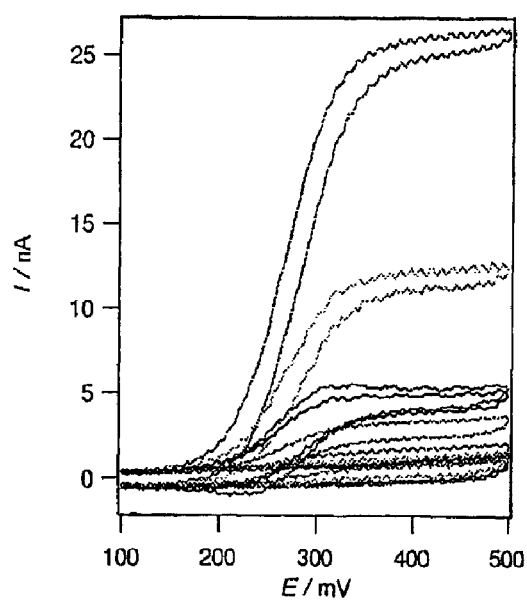
FIG. 9A shows the voltammetric detection of ferrocene carboxylic acid in the microchannel in three electrode mode versus Ag/AgCl (ferrocene carboxylic acid concentration from 0 to 500 µM in 125 mM PBS pH 7.4+KCl 100 mM)
Figure 9B:
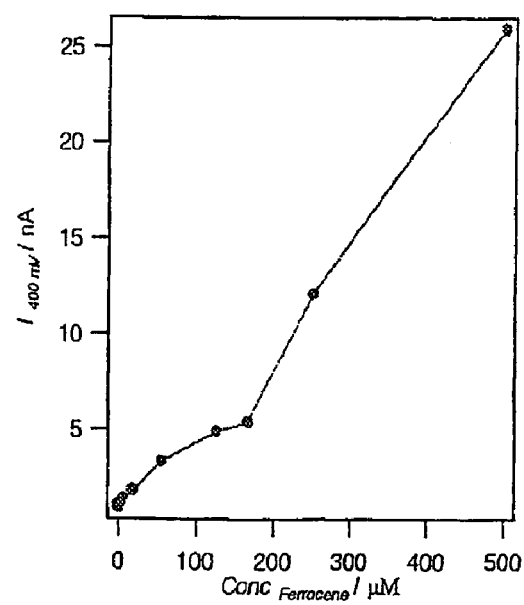
FIG. 9B represents the ferrocene carboxylic acid concentration versus the current at 400 mV vs. Ag|AgCl.

Electrochemical characterisation: The cyclic voltammetric analyses of ferrocene carboxylic acid presented in FIG. 9 exhibits an expected shape for microelectrodes of these dimensions in a microchannel.

A calibration of ferrocene carboxylic acid can be obtained between 0 and 0.5 mM with a slope of 34 pA/µM, which is about 6 times larger than what was obtained in a similar geometry with a 5 times smaller carbon band electrode. The performances of these electrodes are in good agreement with such earlier work and can be used for diagnostics assays.

Figure 10:
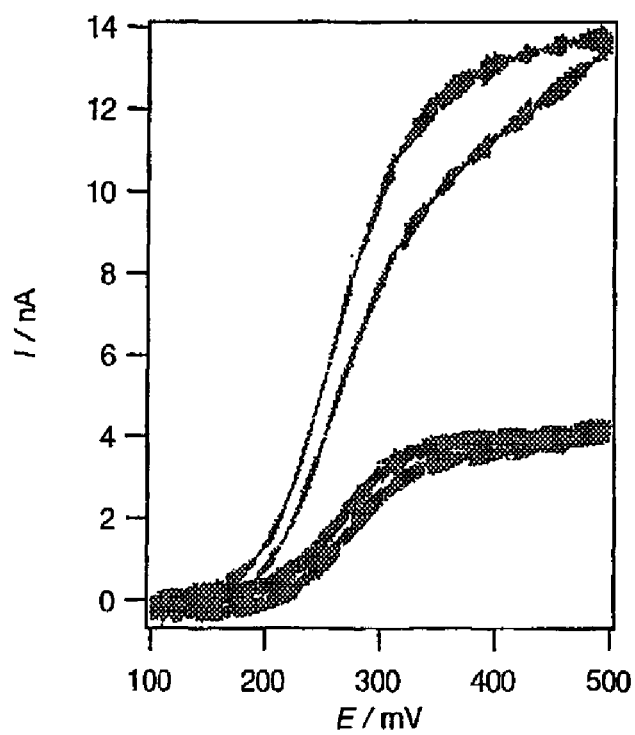
FIG. 10 shows the voltammetric detection of glucose at 15 mM in the microchannel in three electrode mode versus Ag/AgCl (ferrocene carboxylic acid concentration 100 µM in 125 mM PBS pH 7.4+KCl 100 mM)

Glucose detection with plasma etched microchips: In a first experiment the reaction is performed by mixing the enzyme and the mediator solution with a 15 mM glucose solution in a test tube outside the microchip. This solution is then injected in the microchannel and a cyclic voltammetry experiment is performed. The detection of glucose in such microchip can be shown in FIG. 10. Without the presence of glucose in the solution, the voltammogram shows the oxidation of ferrocene carboxylic acid as in FIG. 9. The presence of glucose is revealed by the catalytic shape of the voltammogram, meaning that the mediator is reduced and oxidised by the enzyme and the electrode respectively. This shows that the detection of glucose is possible within this microchannel. It is worth adding that the volume of the micro-channel is about 50 nL in this example.

Figure 11A:
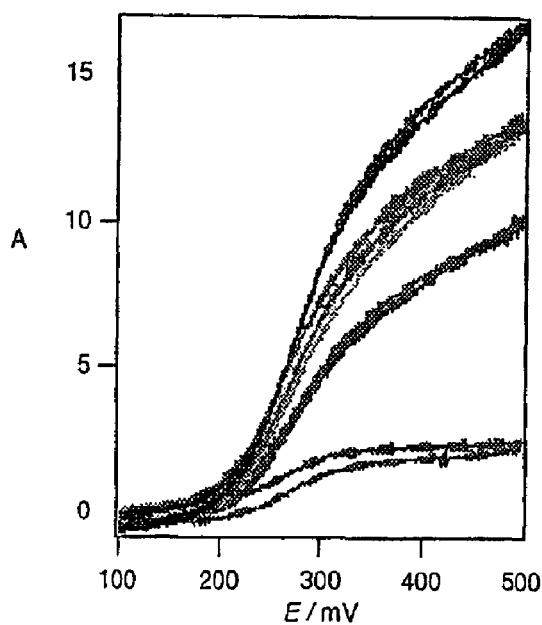
FIG. 11A shows the voltammetric detection of different concentrations of glucose in the microchannel in three electrode mode versus Ag/AgCl (ferrocene carboxylic acid concentration 100 µM in 125 mM PBS pH 7.4+KCl 100 mM)
Figure 11B:
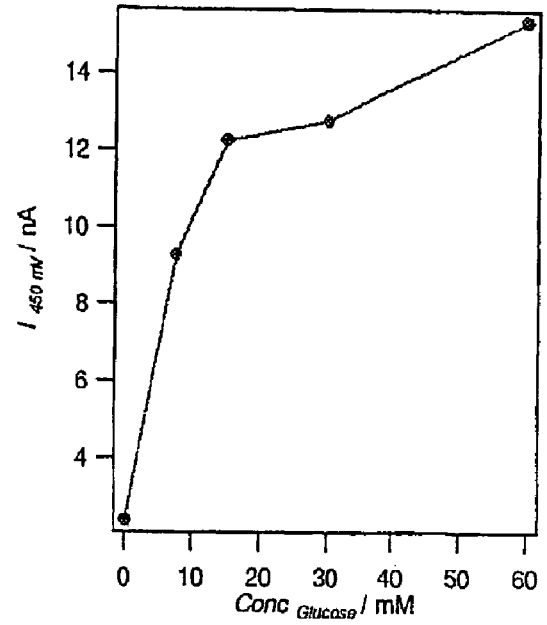
FIG. 11B represents the glucose concentration versus the current at 400 mV vs Ag|AgCl inside the microchannel.

In a second experiment, the glucose oxidase and ferrocene carboxylic acid solution is filled in the microchannel. Solutions of different concentrations of glucose are then deposited on the reservoir at the outlet of the microchannel. The glucose is finally detected by cyclic voltammetry as presented in FIG. 11A. The current detected at 400 mV is also plotted in FIG. 11B against the glucose concentration. A good correlation of the glucose concentration and the detected current is evidenced between 0 and 20 mM. For larger glucose concentrations, the detection reaches a saturation.

Figure 12A:
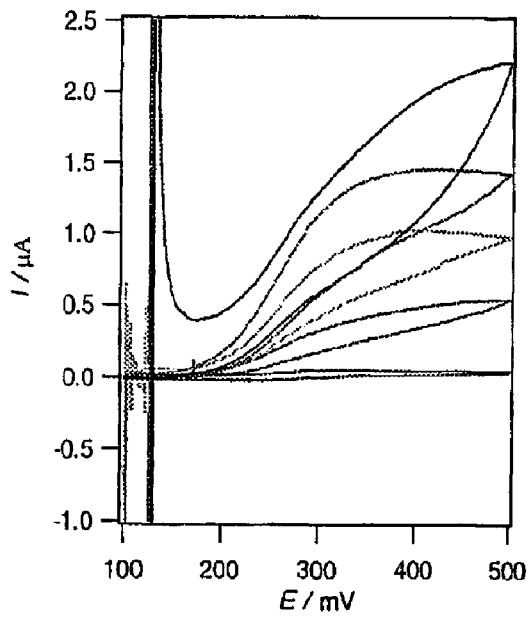
FIG. 12A shows the voltammetric detection of different concentrations of glucose on the pads in three electrode mode versus Ag/AgCl (ferrocene carboxylic acid concentration 100 µM in 125 mM PBS pH 7.4+KCl 100 mM)
Figure 12B:
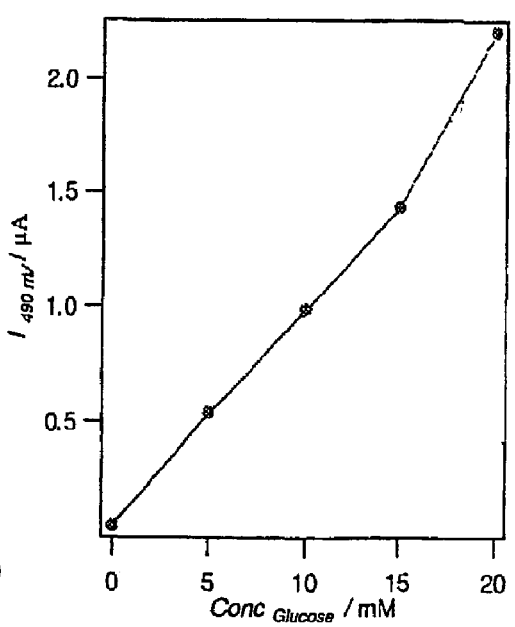
FIG. 12B represents the glucose concentration versus the current at 400 mV vs Ag|AgCl on the electrode pads.

In a third experiment, 2 µL glucose oxidase and ferrocene carboxylic acid is dried on the electrode pads outside of the microchannel. In this experiment, 2 µL solution of glucose is added on the electrode pads and the recorded voltammograms are presented in FIG. 12A. The correlation of the current versus the concentration (FIG. 12B) is linear from 0 to 20 mM. It is interesting to compare the current intensities between the detection inside the microchannel (FIGS. 10 and 11) and on the electrode pads outside of the microchannel. The current is larger in this last experiment because of the difference in the electrode dimension. The volume of detection in this last case is 2 µL versus 50 nL inside the microchannel.

Figure 13:
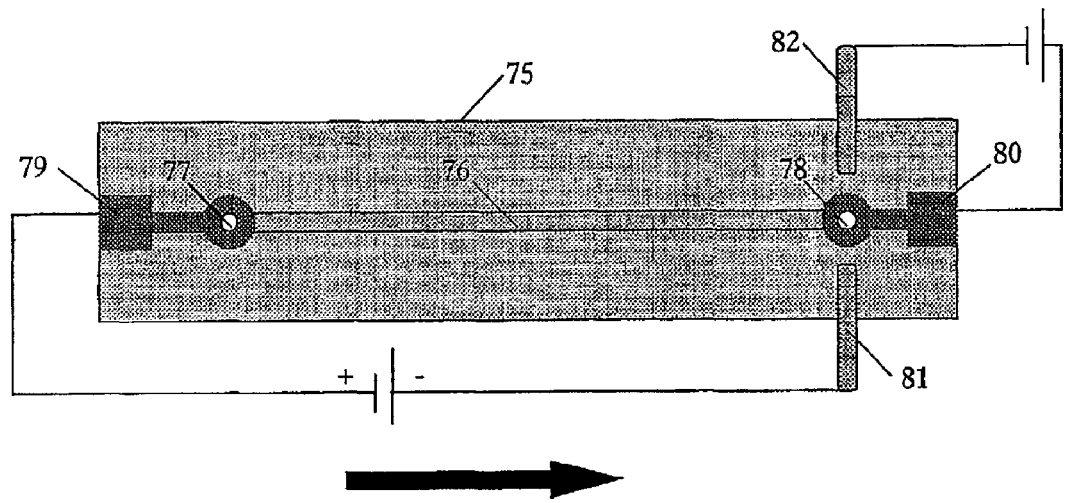
FIG. 13 shows the configuration used here for the electrokinetic pumping at 1100 volts and the simultaneous electrochemical detection. This structure is a top view of the structure presented as a cross section in FIG. 7c.

Another example of application is now shown to demonstrate that the present invention can be used to manufacture micro-structures in which the walls are hydrophilic enough to generate a capillary flow and to control the movement of the fluids by electrical means. To this aim, the device schematically presented in FIG. 13 has been produced in a 50 µm thick polyimide foil 75 following an etching process similar to that described in FIG. 6. The device of FIG. 13 contains a 10 cm long micro-channel 76 with one inlet 77 and one outlet 78 at each extremity. These inlet and outlet also serve as reservoirs, and they are surrounded by two gold coated copper pads 79 and 80 that are used as electrodes. In the outlet reservoir, a platinum electrode 81 and a silver/silverchloride (Ag/AgCl) reference electrode 82 are put in contact with the solution. A high electric field (1100 Volt) is then applied between electrodes 79 and 81, so as to electrokinetically pump the solution through the micro-channel 76 towards the outlet 78. The arrow in FIG. 13 shows the direction of the flow generated by the application of this high voltage. A low potential (for example 400 mV vs Ag/AgCl) can also be applied between electrodes 80 and 82 in order to detect the molecules reaching the outlet reservoir.

Preliminary experiments showed that it is possible to aspirate solution through such microchannels in order to fill and empty them easily. Further experiments have then been undertaken for the characterisation of the electroosmotic flow generated in sealed microchannels of the shape shown in FIG. 13.

Figure 14:
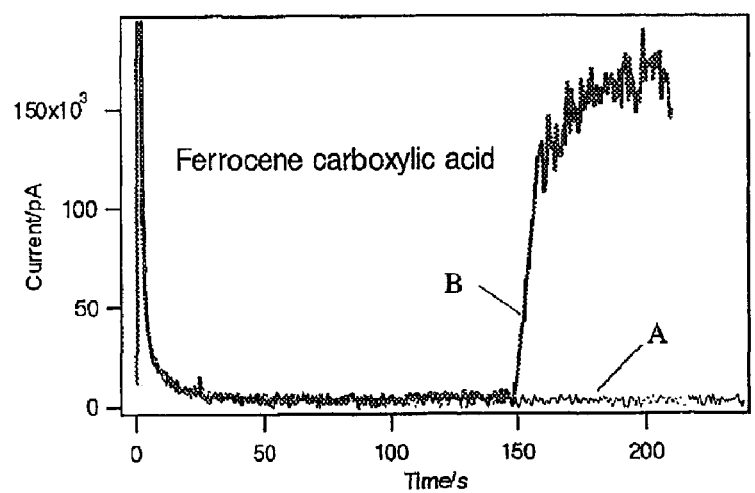
FIG. 14 shows the electrochemical detection of ferrocene carboxylic acid pumped by electroosmotic flow in the device of FIG. 13 (1 mM of ferrocene carboxylic acid in 10 mM phosphate buffer at pH 7.4).

To this aim, a solution of ferrocene carboxylic acid (1 mM of ferrocene carboxylic acid in 10 mM phosphate buffer at pH 7.4) is placed at the inlet of the microchannel and pumped in the direction of the low voltage detection set-up placed at the outlet. As soon as the pumped electroactive species reach the outlet of the microchannel, a current is detected by the electrochemical system defined by electrodes 80 and 82. As shown in FIG. 14, when the solution only contains the phosphate buffer, the current remains close to zero. A current is only detected at the beginning of the experiment, which is an artefact due to the switching of the potential. When the ferrocene carboxylic acid solution is added at the inlet of the micro-channel, the current remains the same as that recorded for the phosphate buffer during 150 seconds. After these 150 seconds, the current rapidly increases until it reaches a plateau after approximately 200 seconds. This clearly shows that the ferrocene carboxilic acid has been electrokinetically pumped through the microchannel, and that it needed approximately 150 seconds to reaach the outlet reservoir. This experiment demonstrates that it is possible to use electroosmotic flow in microsystems produced by the present invention and hence to use them to perform electrophoretic separations as a chromatographic technique.

The three experiments shown here evidence the great interest of using the present structure or kind of structures fabricated by plasma etching for applications in chemical or biological analysis.

Enzyme linked immunosorbent assay (ELISA) with electrochemical detection: In order to develop an immunodiagnostic assay, antibodies can be immobilised on the surface of the channel walls. The procedure is performed on the basis of physisorption or by covalent attachment. Then, standard immunoassay in sandwich or competitive mode can be performed. The detection can be achieved for example by having labeled the secondary antibody or the antigen with an enzyme such as but not limited to HRP, ALP, glucose oxidase, beta-galactosidase, etc. Structures and arrays or networks of structures similar to those shown in FIGS. 6 to 8 can then be used for such immunoassays, since appropriate surface properties can be patterned using the present invention.

Nanospray fabrication: The structure fabricated and presented in FIG. 7 can be used for mass spectrometry analysis. Indeed, if the structure is cut either with a knife, a laser or by plasma, the cross section of the channel can be placed in front of a mass spectrometer inlet, and the high voltage required to spray the solution out of the capillary can be applied thank to the electrode fabricated inside the capillary. The interior of the channel (that is hydrophilic) serves to let the channel be filled and the outlet of the channel (that is hydrophobic) serves to favor the fabrication of the Taylor cone. Indeed, the exterior must be hydrophobic to prevent the aqueous solution to spread outside of the channel, thereby favoring the generation of the spray.

These examples demonstrate the use of the present invention even if it is not limited to these applications.

What is claimed is:

1. A method for manufacturing a microfluidic device having a micro-system, said method comprising the steps of:
providing a multilayer body, said multilayer body comprising at least one polymer layer coated with at least one protective layer;
forming a recess in said protective layer; and
structuring said polymer layer to form a micro-structure in said polymer layer by dry etching said polymer layer at the place of said recess in a manner that a wall of said micro-structure has a first part having a hydrophobic surface and a second part having a hydrophilic surface, whereby said micro-structure forms the micro-system for performing an analysis using electrochemical fluid properties.

2. The method according to claim 1, wherein said polymer layer is etched by one selected from the group consisting of plasma etching, photoablation and a combination thereof.

3. The method according to claim 1, wherein said micro-structure comprises a micro-channel.

4. The method according to claim 1, wherein said micro-structure comprises a micro-channel and an opening.

5. The method according to claim 1, wherein at least one micro-channel which is essentially parallel to a surface of said polymer layer is formed.

6. The method according to claim 1, wherein at least one micro-channel which is essentially perpendicular to a surface of said polymer layer is formed.

7. The method according to claim 1, further comprising the step of:
removing partially or totally said protective layer after the structuring step.

8. The method according to claim 1, wherein a plurality of micro-structures are formed simultaneously.

9. The method according to claim 1, wherein said micro-structure has a thickness corresponding to the entire thickness of said polymer layer.

10. The method according to claim 1, wherein said polymer layer is structured using a plurality of etching steps.

11. The method according to claim 1, wherein said multilayer body comprises a plurality of polymer layers, and said micro-channel has a thickness corresponding to the entire thickness of at least one of said plurality of polymer layers.

12. The method according to claim 1, wherein said multilayer body contains means for assembling said polymer layer in a precise relative position for desired alignment of said micro-structure.

13. The method according to claim 1, wherein said micro-structure has at least one dimension in the range of about 0.1 to about 1000 micrometer (m).

14. The method according to claim 1, wherein said polymer layer has maximum thickness of about 1 centimeter.

15. The method according to claim 1, wherein said multilayer body is further comprised of a plurality of layers comprising a first layer with hydrophilic surface properties and a second layer with hydrophobic surface properties.

16. The method according to claim 1, wherein said multilayer body comprises a plurality of polymer layers, and at least two of said plurality of polymer layers are etched simultaneously.

17. The method according to claim 1, wherein the forming step is at least partially done with the aid of a computer printer.

18. The method according to claim 1, wherein the etching step is followed by derivatisation of the surface of the etched micro-structure by pouring the multilayer body into a solution containing a reagent for said a derivatisation.

19. The method according to claim 1, wherein the etching step is followed by immobilisation of a material on the etched micro-structure by pouring the multilayer body into a solution containing a reagent for said immobilisation.

20. The method according to claim 1, wherein said multilayer body comprises a plurality of polymer layers, and surface properties of said micro-structure are dependent upon surface properties of said plurality of polymer layers.

21. The method according to claim 1, wherein the structuring step is further comprised of sequential etching steps to fabricate three-dimensional features in said multilayer body.

22. The method according to claim 1, wherein said micro-structure comprises an opening.

23. The method according to claim 22 wherein said opening constitutes one selected from the group consisting of a reservoir, a fluid reservoir, a reaction chamber, a well, an access hole and a combination thereof.

24. The method according to claim 1, wherein said protective layer is made of an electrically conductive material.

25. The method according to claim 24, further comprising the step of:
providing the electrically conductive protective layer with leads for connection to a source of electrical power, wherein said electrically conductive material serves as an electrode.

26. The method according to claim 1, wherein said polymer layer is etched under a plurality of atmospheres.

27. The method according to claim 26, wherein said atmospheres are selected from the group consisting of air, oxygen, nitrogen, hydrogen, argon, and fluor.

28. The method according to claim 1, further comprising the step of immobilizing at least one affinity agent on the etched micro-structure.

29. The method according to claim 28, wherein said affinity agent is selected from the group consisting of an antigen, an antibody, an enzyme, a peptide and DNA.

30. The method according to claim 28, wherein said immobilizing step comprises the step of pouring the multilayer body into a solution containing said affinity agents.

31. The method according to claim 1, further comprising the step of:
adding at least one supplementary layer to said multilayer body after the structuring step.

32. The method according to claim 31, wherein said supplementary layer is added by lamination, adhesive addition, pressure application or bonding after treatment by exposition to a plasma.

33. The method according to claim 31, wherein said supplementary layer is designed in a manner that said supplementary layer covers said micro-structure so as to form a sealed micro-channel with at least one access hole connected to said micro-channel.

34. The method according to claim 31, wherein said supplementary layer covers a plurality of micro-structures so as to form interconnected micro-channels.

35. The method according to claim 31, wherein said supplementary layer before being added to said multilayer body already contains at least one micro-structure.

36. The method according to claim 35, wherein said supplementary layer covers said micro-structures so as to form sealed micro-channels with at least one access hole connected to said micro-channels.

37. The method according to claim 1, further comprising the step of modifying surface properties of at least one layer of said multilayer body.

38. The method according to claim 37, wherein the modifying step comprises the step of depositing a metal on at least one portion of said at least one layer of said multilayer body.

39. The method according to claim 38, wherein said step of depositing a metal on at least one portion of said at least one layer of said multilayer body creates at least one electrode placed in one wall of said micro-structure.

40. The method according to claim 37, wherein the modifying step comprises the step of performing a polymerization reaction.

41. The method according to claim 40, wherein said micro-structure ends in a tip shape.

* * * * *